(12) United States Patent
Aquino et al.

(10) Patent No.: US 11,958,797 B2
(45) Date of Patent: Apr. 16, 2024

(54) PROCESS FOR THE PREPARATION OF INTERMEDIATES FOR THE SYNTHESIS OF VITAMIN A DERIVATIVES FROM POLYENES BY CYCLISATION

(71) Applicant: DSM IP ASSETS B.V., Heerlen (NL)

(72) Inventors: Fabrice Aquino, Kaiseraugst (CH); Werner Bonrath, Kaiseraugst (CH); Marc-André Mueller, Kaiseraugst (CH); Bettina Wuestenberg, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 330 days.

(21) Appl. No.: 17/603,177

(22) PCT Filed: Apr. 3, 2020

(86) PCT No.: PCT/EP2020/059481
§ 371 (c)(1),
(2) Date: Oct. 12, 2021

(87) PCT Pub. No.: WO2020/212165
PCT Pub. Date: Oct. 22, 2020

(65) Prior Publication Data
US 2022/0204434 A1 Jun. 30, 2022

(30) Foreign Application Priority Data
Apr. 15, 2019 (EP) ..................................... 19169204

(51) Int. Cl.
*C07C 49/21* (2006.01)
*C07C 45/67* (2006.01)

(52) U.S. Cl.
CPC ............. *C07C 49/21* (2013.01); *C07C 45/67* (2013.01); *C07C 2601/16* (2017.05)

(58) Field of Classification Search
CPC .............................. C07C 49/21; C07C 45/67
See application file for complete search history.

(56) References Cited

U.S. PATENT DOCUMENTS

| 3,238,260 | A | 3/1966 | Pasedach et al. |
| 7,141,698 | B2 | 11/2006 | Dobler et al. |
| 2006/0014984 | A1 | 1/2006 | Dobler et al. |
| 2007/0189984 | A1 | 8/2007 | Wolber et al. |
| 2010/0063325 | A1 | 11/2010 | Bonrath et al. |
| 2010/0312016 | A1 | 12/2010 | Luettin et al. |

FOREIGN PATENT DOCUMENTS

| JP | H0640992 | 2/1994 |
| JP | 2002-322145 | 11/2002 |
| JP | 2006-505597 | 2/2006 |
| JP | 2010-509255 | 3/2010 |
| JP | 2010-521509 | 6/2010 |
| WO | WO 2008/055704 | 5/2008 |
| WO | WO 2008/113545 | 9/2008 |

OTHER PUBLICATIONS

L.P. Davydova, et al., "Synthetic investigations on the chemistry of polyenic compounds. XXXVI. Synthesis of 7,8-dihydroretinoic acid and allied Compounds", Journal of General Chemistry of the USSR, vol. 43, 1973, pp. 2047-2052 (6 pages).
Jinchul Kuk, et al., "General Preparation and Controlled Cyclization of Acyclic Terpenoids", Journal of Organic Chemistry, vol. 73, No. 5, 2008, 35 pages.
Yun Zhu, et al., "FT-IR spectra of all sixteen isomers of retinal, their isolation, and other spectroscopic properties.", Tetrahedron, vol. 48, No. 46, 1992, pp. 10061-10074 (14 pages).
International Search Report and Written Opinion of the ISA for PCT/EP2020/059481 dated Jun. 17, 2020, 15 pages.
The First Office Action, CN Application No. 202080028214.3, dated Dec. 2, 2022.

*Primary Examiner* — Sikarl A Witherspoon
(74) *Attorney, Agent, or Firm* — NIXON & VANDERHYE P.C.

(57) ABSTRACT

The application relates to a process for the preparation of a compound of formula (II) by cyclisation of a polyene of formula (I), and to an intermediate of formula (III). The obtained compounds are useful intermediates in the preparation of specific isoprenoids, preferably in the production of vitamin A and derivatives of vitamin A.

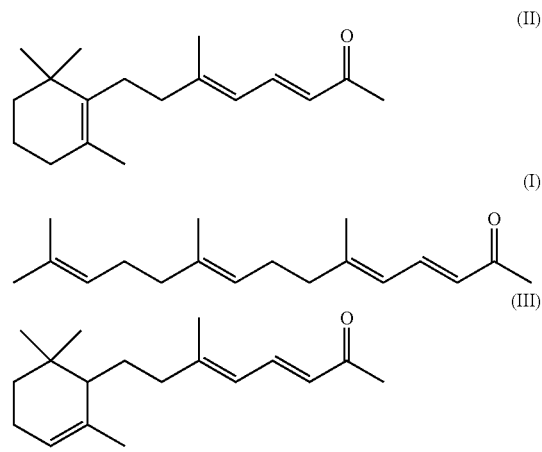

14 Claims, No Drawings

PROCESS FOR THE PREPARATION OF INTERMEDIATES FOR THE SYNTHESIS OF VITAMIN A DERIVATIVES FROM POLYENES BY CYCLISATION

This application is the U.S. national phase of International Application No. PCT/EP2020/059481 filed Apr. 3, 2020 which designated the U.S. and claims priority to EP Patent Application No. 19169204.5 filed Apr. 15, 2019, the entire contents of each of which are hereby incorporated by reference.

The present invention relates to a cyclisation process of specific polyenes. The obtained compounds, which comprise a carbon ring are useful intermediates in the organic syntheses (for example in the production of specific isoprenoids, preferably in the production of vitamin A and derivatives of vitamin A).

Due to the importance of vitamin A (and derivatives of vitamin A) and the complexity of its synthesis there is always a need for improving the synthesis of vitamin A (and derivatives of vitamin A) and/or finding alternative routes to produce vitamin A (and derivatives of vitamin A).

Surprisingly, it was found that it is possible to cyclisize the compound of formula (I)

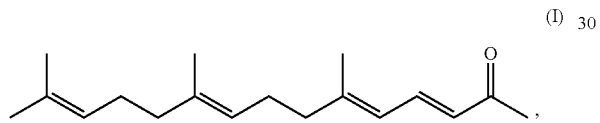
(I)

which results in useful intermediates for organic synthesis (especially of the production of vitamin A and/or its derivatives).

Therefore, the present invention relates to the cyclisation of a compound of formula (I)

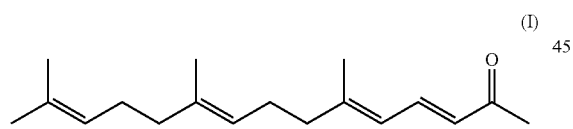
(I)

in the presence of an acid.

The main product of this reaction is the compound of formula (II)

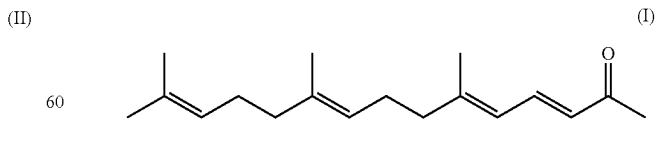
(II)

Compound of formula (II) is an important intermediate in the production of specific isoprenoids (especially of vitamin A and its derivatives).

The cyclisation reaction of the present invention also provides the following products (compounds of formula (III), (IV) and (V)):

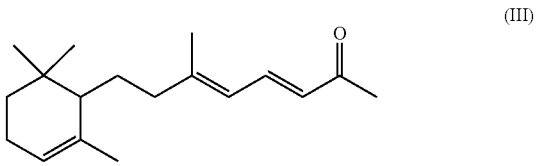 [SMILES: CC(=O)/C=C/C=C(\C)CCC1C(C)=CCCC1(C)C]
(III)

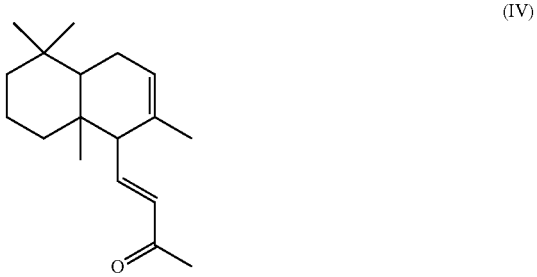
(IV)

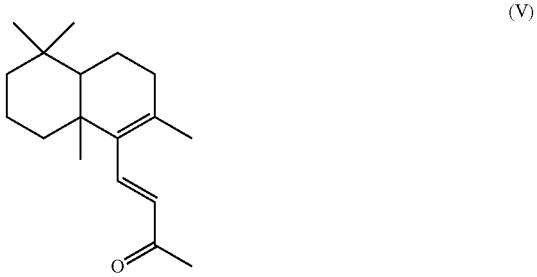
(V)

Surprisingly, it is possible (by the process of the present invention) to keep the amounts of the side products low and therefore produce the main product (compound of formula (II)) in a high amount.

Surprisingly, this is achieved by the use of at least one strong Brønsted acid in the process according to the present invention.

Therefore, the present invention relates a process (P) for to the production of a compound of formula (II)

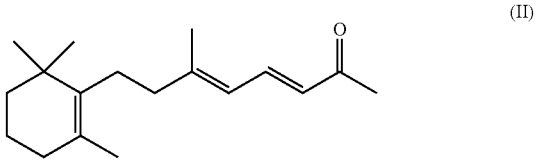 [SMILES: CC(=O)/C=C/C=C(\C)CCC1=C(C)CCCC1(C)C]
(II)

by cyclisation of a compound of formula (I)

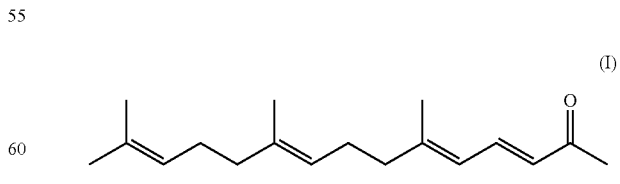
(I)

in the presence of at least one strong Brønsted acid.

The strong Brønsted acid can be solid as well as liquid.

Examples of solid strong Brønsted acid are ion-exchange resins, which have usually sulfonic acid groups, e.g. sodium polystyrene sulfonate or polyAMPS, A further example of solid acid catalysts useful for this cyclisation reaction are alkylsulphinic acid on a carrier such as silica.

Typical examples of such ion-exchange resins are i.e. Amberlyst® 15, Amberlyst® 16 and Amberlyst® 36 and Deloxan ASP 1/9.

It is also possible to use a liquid acid, which has a $Pk_a$ value similar to sulfonic acids.

Preferred liquid acids are those of formula (VI)

   (VI), wherein R is $C_1$-$C_4$-alkyl, Cl, $CH_3$ or $CF_3$.

It is also possible to use a liquid acid, which is preferably a compound of formula (VI)

   (VI), wherein R is $C_1$-$C_4$-alkyl, Cl, $CH_3$ or $CF_3$.

The preferred liquid acids are $CH_3SO_3H$, $ClSO_3H$ and $CF_3SO_3H$. The most preferred liquid acid is $CH_3SO_3H$.

Therefore, the present invention also relates to a process (P1), which is process (P), wherein the acid is a solid acid.

Therefore, the present invention also relates to a process (P1'), which is process (P1), wherein the acid is an ion-exchange resin, which has sulfonic acid groups.

Therefore, the present invention also relates to a process (P2), which is process (P), wherein the acid is a liquid acid.

Therefore, the present invention also relates to a process (P2'), which is process (P2), wherein the acid is a compound of the following formula (VI)

   (VI), wherein R is $C_1$-$C_4$-alkyl, Cl, $CH_3$ or $CF_3$.

Therefore, the present invention also relates to a process (P2"), which is process (P2) or (P2'), wherein the acid is chosen from the group consisting of $CH_3SO_3H$, $ClSO_3H$ and $CF_3SO_3H$.

Therefore, the present invention also relates to a process (P2'''), which is process (P2), (P2') or (P2"), wherein the liquid acid is $CH_3SO_3H$.

The acid, which is used in the process according to the present invention is used in an amount of 0.5 mol-equivalent (in view of the compound of formula (I)) up to 10 mol-equivalent (in view of the compound of formula (I)).

Preferably, the amount of the acid is 0.5-8 mol-equivalent (in view of the compound of formula (I)).

Therefore, the present invention also relates to a process (P3), which is process (P), (P1), (P1'), (P2), (P2'), (P2") or (P2'''), wherein the acid is used in an amount of 0.5 mol-equivalent (in view of the compound of formula (I)) up to 10 mol-equivalent (in view of the compound of formula (I)).

Therefore, the present invention also relates to a process (P3'), which is process (P), (P1), (P1'), (P2), (P2'), (P2") or (P2'''), wherein the acid is used in an amount of 0.5-8 mol-equivalent (in view of the compound of formula (I)).

The process according to the present invention can be carried out in the presence of at least one inert solvent. Suitable solvents are polar aprotic solvents such as $CH_2Cl_2$.

Therefore, the present invention also relates to a process (P4), which is process (P), (P1), (P1'), (P2), (P2'), (P2"), (P2'''), (P3) or (P3'), wherein the process is carried out in the presence of at least one inert solvent.

Therefore, the present invention also relates to a process (P4'), which is process (P4), wherein the process is carried out in at least one polar aprotic solvent.

Therefore, the present invention also relates to a process (P4"), which is process (P4), wherein the process is carried out in $CH_2Cl_2$.

The process according to the present invention is usually carried out at a temperature of from −50° C. to about 50° C. Preferably at a temperature of from −40° C. to about 40° C.

Therefore, the present invention also relates to a process (P5), which is process (P), (P1), (P1'), (P2), (P2'), (P2"), (P2'''), (P3), (P3'), (P4), (P4') or (P4"), wherein the process is carried out at a temperature of from −50° C. to 50° C.

Therefore, the present invention also relates to a process (P5'), which is process (P), (P1), (P1'), (P2), (P2'), (P2"), (P2'''), (P3), (P3'), (P4), (P4') or (P4"), wherein the process is carried out at a temperature of from −40° C. to 40° C.

The process according to the present invention is usually carried out at a residence time ($\tau$) of 5-30 minutes, preferably 10-20 minutes.

Therefore, the present invention also relates to a process (P6), which is process (P), (P1), (P1'), (P2), (P2'), (P2"), (P2'''), (P3), (P3'), (P4), (P4'), (P4"), (P5) or (P5'), wherein the process is carried out at a residence time ($\tau$) of 5-30 minutes.

Therefore, the present invention also relates to a process (P6'), which is process (P), (P1), (P1'), (P2), (P2'), (P2"), (P2'''), (P3), (P3'), (P4), (P4'), (P4"), (P5) or (P5'), wherein the process is carried out at a residence time ($\tau$) of 10-20 minutes.

The process according to the present invention can be carried out batch-wise as well as continuously.

Therefore, the present invention also relates to a process (P7), which is process (P), (P1), (P1'), (P2), (P2'), (P2"), (P2'''), (P3), (P3'), (P4), (P4'), (P4"), (P5), (P5'), (P6) or (P6'), wherein the process is carried out batch-wise.

Therefore, the present invention also relates to a process (P7'), which is process (P), (P1), (P1'), (P2), (P2'), (P2"), (P2'''), (P3), (P3'), (P4), (P4'), (P4"), (P5), (P5'), (P6) or (P6'), wherein the process is carried out continuously The compound of formula (II) is obtained in significantly higher amount than the other products of the cyclisation process.

The obtained other products (compounds of formula (III), (IV) and (V)) can be removed easily from the compound of formula (II).

Furthermore, the product (III)

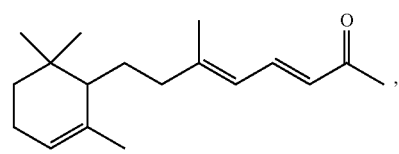

which is obtained in a higher amount than the other product (IV), (V) is not known.

Therefore, the present invention also relates to a compound of formula (III)

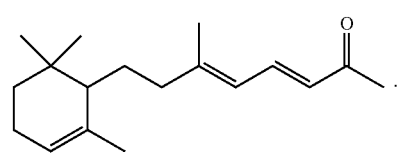

It is possible to convert the compound of formula (III) into the compound (II) in an easy and simple way (by acid treatment at a slightly increased reaction time)

The following examples serve to illustrate the invention. The temperature is given in ° C. and all percentages are related to the weight.

EXAMPLES

Example

Example 1

17.7 g (0.18 mol) of methane sulfonic acid is mixed with Dichloromethane (40 ml) and cooled to −38° C.

8.8 g (0.034 mol) of compound of formula (I) is added under stirring in a period of 10 minutes.

The mixture is stirring another 15 min at −30 to −39° C.

The reaction mixture is quenched in 80 ml water and extracted with 80 ml t-BME. Layers were separated.

The water layer is extracted with 2×40 ml t-BME and the organic layer is washed with 40 ml water.

The organic layer neutralized with 5 ml Et$_3$N (pH: 9) and then washed with 50 ml water.

After separation of the layers, the organic phase is dried on Na$_2$SO$_4$ and concentrated on a rotavapor.

The overall yield of the compound of formula (II) was 44%.

The invention claimed is:

1. Process for the production of a compound of formula (II)

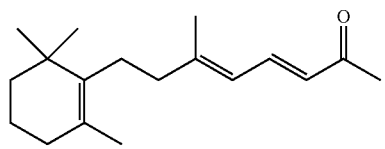
(II)

by cyclisation of a compound of formula (I)

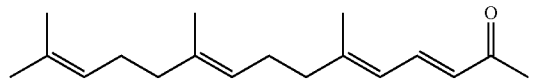
(I)

in the presence of at least one strong Brønsted acid.

2. Process according to claim 1, wherein the acid is a solid acid.

3. Process according to claim 1, wherein the acid is an ion-exchange resin, which has sulfonic acid groups.

4. Process according to claim 1, wherein the acid is a liquid acid.

5. Process according to claim 1, wherein the acid is a compound of the following formula (VI)

$$R\text{—}SO_3H \quad\quad\quad (VI),$$

wherein R is C$_1$-C$_4$-alkyl, Cl, CH$_3$ or CF$_3$.

6. Process according to claim 1, wherein the acid is chosen from the group consisting of CH$_3$SO$_3$H, ClSO$_3$H and CF$_3$SO$_3$H.

7. Process according to claim 1, wherein the acid is used in an amount of 0.5 mol-equivalent (in view of the compound of formula (I)) up to 10 mol-equivalent (in view of the compound of formula (I)).

8. Process according to claim 1, wherein the process is carried out in the presence of at least one inert solvent.

9. Process according to claim 1, wherein the process is carried out in at least one polar aprotic solvent.

10. Process according to claim 1, wherein the process is carried out at a temperature of from −50° C. to 50° C.

11. Process according to claim 1, wherein the process is carried out at a residence time (□) of 5-30 minutes.

12. Process according to claim 1, wherein the process is carried out batch-wise.

13. Process according to claim 1, wherein the process is carried out continuously.

14. A compound of formula (III)

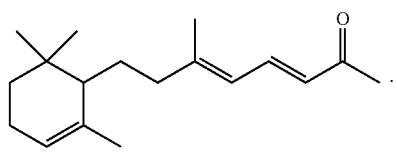
(III)

\* \* \* \* \*